(12) United States Patent
Cabrera et al.

(10) Patent No.: US 6,398,962 B1
(45) Date of Patent: Jun. 4, 2002

(54) USE OF MONOLITHIC SORBENTS FOR PREPARATIVE CHROMATOGRAPHIC SEPARATION

(75) Inventors: Karin Cabrera, Dreieich; Dieter Lubda, Bensheim; Michael Schulte, Rüsselsheim; Andreas Meudt, Flörsheim, all of (DE); Olivier Ludemann-Hombourger, Vandoeuvre-lès-Nancy (FR); Gerhard Wieland, Bensheim (DE); Kristina Czerny, Weiterstadt (DE); Axel Delp, Fränkisch-Crumbach (DE); Edith Dicks, Darmstadt (DE); Alexander Kraus, Griesheim (DE)

(73) Assignee: Merck KGaA, Darmstadt (DE)

( * ) Notice: Subject to any disclaimer, the term of this patent is extended or adjusted under 35 U.S.C. 154(b) by 0 days.

(21) Appl. No.: 09/445,585

(22) PCT Filed: Jun. 12, 1998

(86) PCT No.: PCT/EP98/03546
§ 371 (c)(1), (2), (4) Date: May 19, 2000

(87) PCT Pub. No.: WO98/58253
PCT Pub. Date: Dec. 23, 1998

(30) Foreign Application Priority Data

| Jun. 18, 1997 | (DE) | 197 25 639 |
| Jun. 20, 1997 | (DE) | 197 26 152 |
| Jun. 20, 1997 | (DE) | 197 26 151 |
| Jan. 19, 1998 | (DE) | 198 01 575 |

(51) Int. Cl.$^7$ .............................................. B01D 15/08
(52) U.S. Cl. ...................... 210/635; 210/656; 210/198.2
(58) Field of Search ................................. 210/635, 656, 210/659, 198.2

(56) References Cited

U.S. PATENT DOCUMENTS

| 4,333,770 A | * | 6/1982 | Neuzil | 210/674 |
| 4,533,398 A | * | 8/1985 | Neuzil | 210/674 |
| 5,399,535 A | | 3/1995 | Whitman | 501/80 |
| 5,624,875 A | * | 4/1997 | Nakanishi | 501/39 |

FOREIGN PATENT DOCUMENTS

| WO | 95 03256 | 2/1995 | 210/198.2 |

OTHER PUBLICATIONS

Minakuchi et al: "Effect of skeleton size on the performance of octadecylsilyated continuous porous silica columns in reverse phase liquid chromatography" Journal of Chromatography, Bd. 762, Nr. 1,21. Feb. 1997 PP> 135–146.

* cited by examiner

Primary Examiner—Ernest G. Therkorn
(74) Attorney, Agent, or Firm—Millen, White, Zelano & Branigan, P.C.

(57) ABSTRACT

The invention relates to use of monolithic sorbents for preparative separation processes, specially for processes according to the simulated moving bed (SMB) principle.

17 Claims, 5 Drawing Sheets a)
b)

a)

b)

c)

USE OF MONOLITHIC SORBENTS FOR PREPARATIVE CHROMATOGRAPHIC SEPARATION

REFERENCE TO RELATED APPLICATIONS

This application is a 371 of PCT/EP98/03546 filed Jun. 12, 1998.

The invention relates to the use of monolithic sorbents, particularly ones containing separation effectors, for preparative chromatographic separation processes, and also to a process for the preparative chromatographic separation of at least two substances using monolithic sorbents.

The aim of preparative chromatographic separation processes is the isolation of the purified substance. In contrast thereto, analytical chromatographic separation processes are directed at a high selectivity at a low bandwidth. Analytic processes do not serve for the isolation of the substance and additional analytical procedures (e.g. mass spectrometry, UV/VIS spectrometry) follow the separation process. For preparative chromatographic separation processes, the optimum compromise between chromatographic resolution and productivity is important.

To achieve good economics for preparative material separations, it is important to achieve high flow rates and short elution times and to maintain moderate operating pressures. The separation performance of a chromatographic column is characterized by the theoretical plate height (or number of theoretical plates per metre). The relationships to flow and diffusion processes are described by the van Deemter equation. If the diameter of the sorbent particles is increased, the number of theoretical plates decreases and the column has to be made longer so as not to reduce the separation performance. If the diameter of the sorbent particles is increased, the number of theoretical plates becomes relatively strongly dependent on the flow rate. Thus, the achievable chromatographic separation performance is in many cases greatly dependent on the flow rate selected (steep H(u) curve). The relationships mentioned are basically known to a person skilled in the art and are described in manuals such as "Handbuch der HPLC" (K.K. Unger, ed.; GIT-Verlag, Darmstadt, DE). In contrast thereto, it has been found that in the use according to the invention of monolithic sorbents, the pore diameter of the macropores can be varied without the dimensions of the skeleton phase located between the macropores having to be varied. As a result, the pressure drop can be reduced by choice of a sorbent having larger macropores while the increased flow rate barely influences the separation performance.

In preparative material separations, countercurrent processes have become important. Since it is technically very difficult to achieve actual movement of a stationary phase, the movement of the stationary phase is simulated. For this purpose, the overall column bed is divided into individual columns which are cyclically connected in series. The total number of columns is typically a multiple of four, since such a system has four chromatographic zones. After a defined time, the lines are switched around, which simulates movement of the column bed in the opposite direction. Further details regarding the mode of operation of SMB chromatography may be found, for example, in WO 97/47 617. For continuous "simulated moving bed" chromatography (SMB chromatography), particulate sorbents are customarily used as separation materials. The column packings used do not allow optimum flow rates, since the operating pressure is very high for particulate supports. Furthermore, the mechanical stability of the particulate sorbent beds is not very good. In addition, SMB chromatography requires a series of chromatographic columns (typically up to 24) having virtually identical properties to be provided. In the case of particulate sorbent beds, this can be achieved only with great effort when packing the columns and with selection of the packed columns.

It is an object of the invention to provide chromatographic preparative separation processes, in particular for the SMB method, which have high flow rates at a moderate operating pressure.

It has been found that monolithic sorbents can be used for separation processes operating at high flow rates; thus, a higher throughput per unit time, i.e. improved productivity, can be achieved. The productivity achievable in separation processes according to the invention using monolithic sorbents is typically an order of magnitude higher than in separation processes using particulate sorbents.

The invention provides a process for the preparative chromatographic separation of at least two substances, especially by the SMB method, wherein the stationary phase used is a monolithic sorbent based on shaped $SiO_2$ bodies whose macropores have diameters in the range from 2 to 20 µm and whose mesopores have diameters in the range from 2 to 100 nm (in each case median values).

DESCRIPTION OF THE PREFERRED EMBODIMENTS

Figure 1:
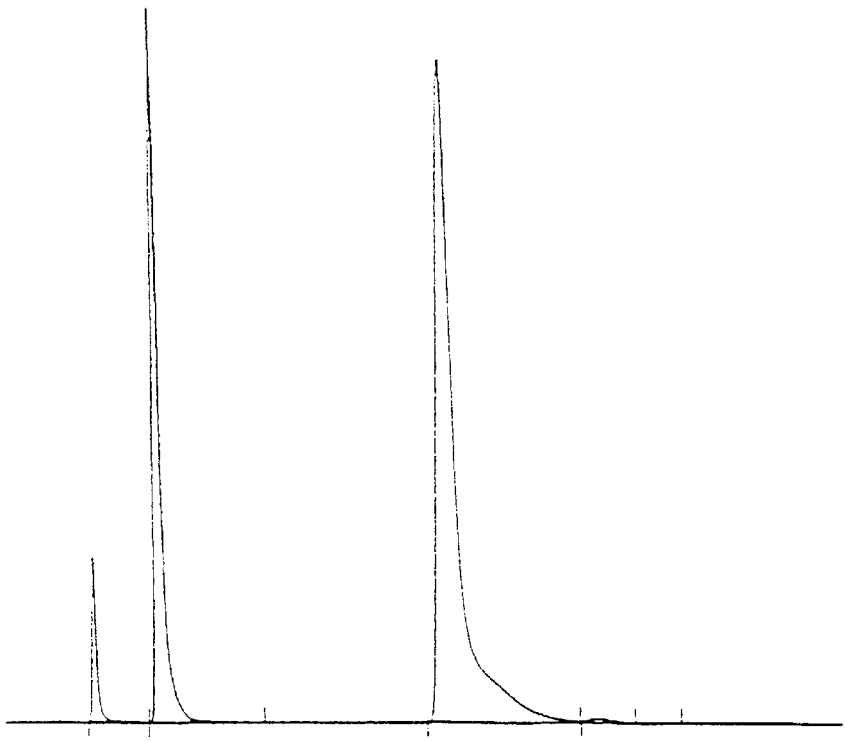
FIGS. 1 and 2 show separations of toluene, 2-and 3-nitroacetanilide over two unmodified monolithic sorbents having different pore sizes of the macropores.
Figure 2:
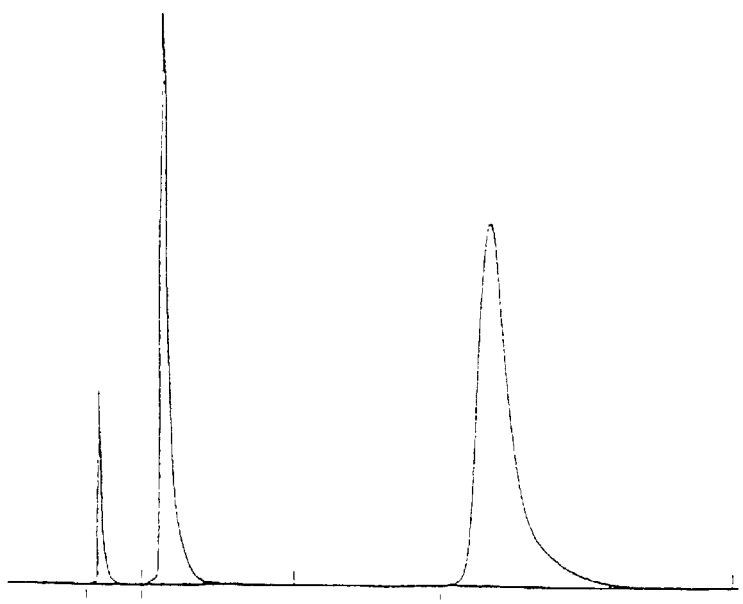
Figure 3:
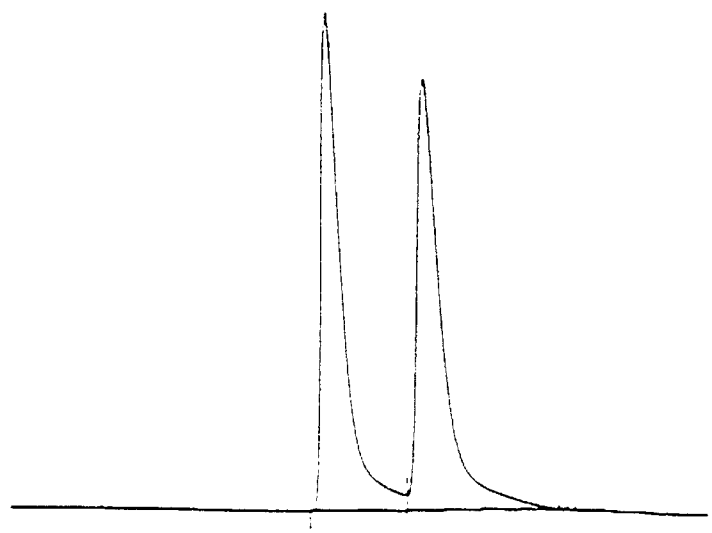
FIG. 3 shows separation of enantiomers on a chiral monolithic sorbent.
Figure 4:
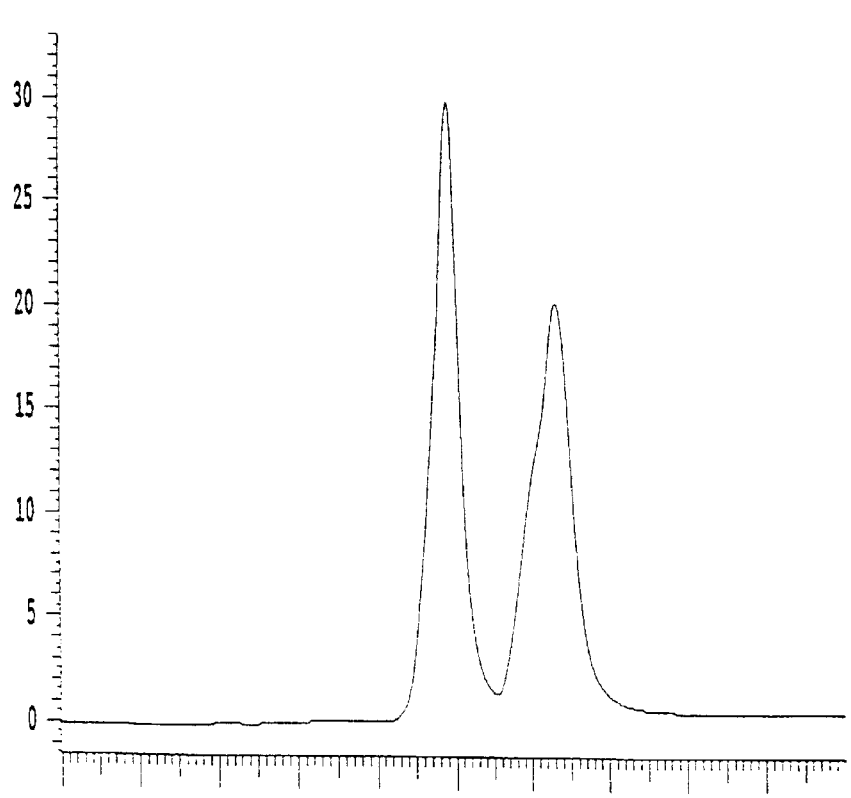
FIG. 4 shows the resolution of racemic chromakalim over a sorbent containing chemically bound beta-cyclodextrin.
Figure 5:
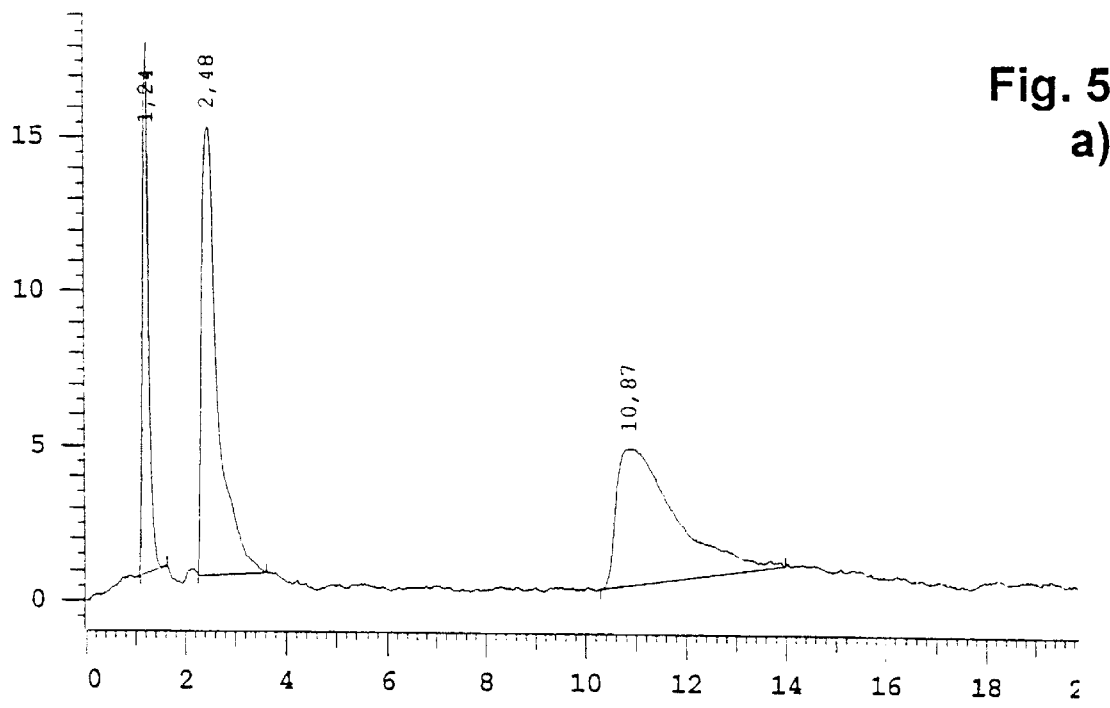
FIGS. 5A, 5B, and 5C show separations of toluene, 2-nitroacetanilide, 3-nitroacetanilide at different flow rates.
Figure 5:
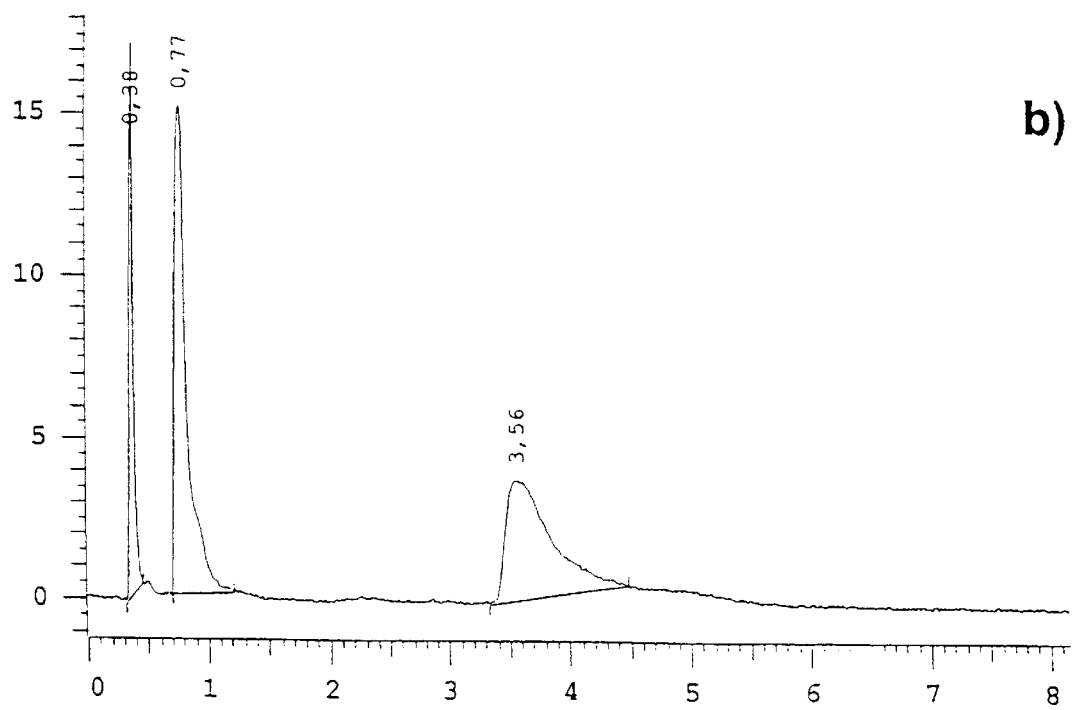
Figure 5:
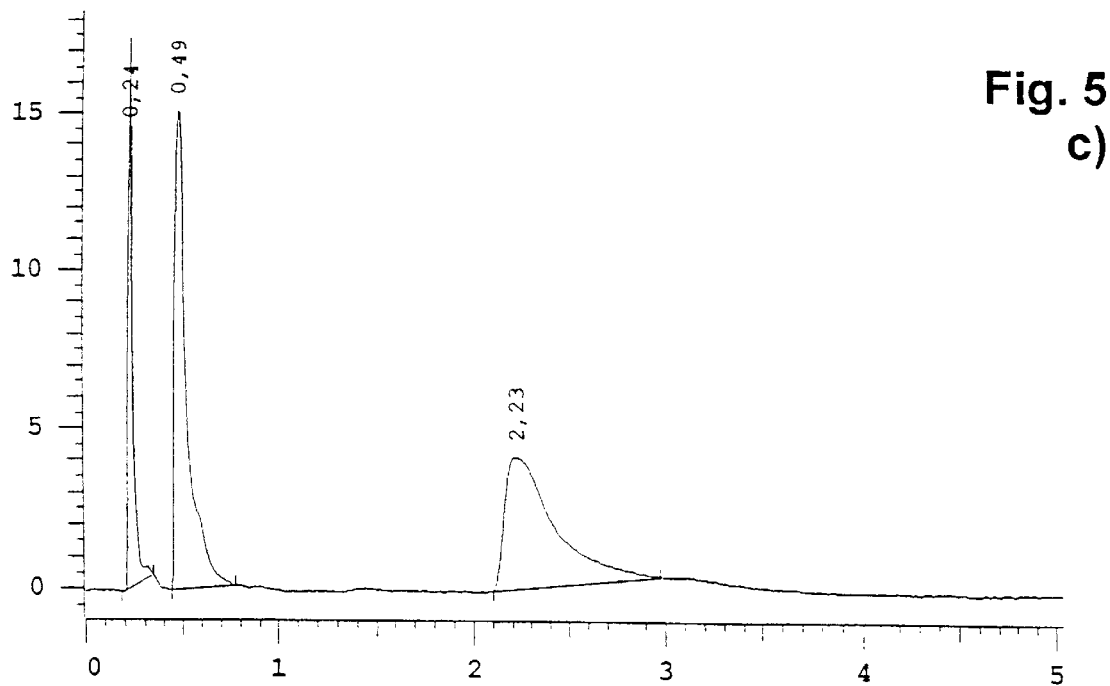
Figure 6:
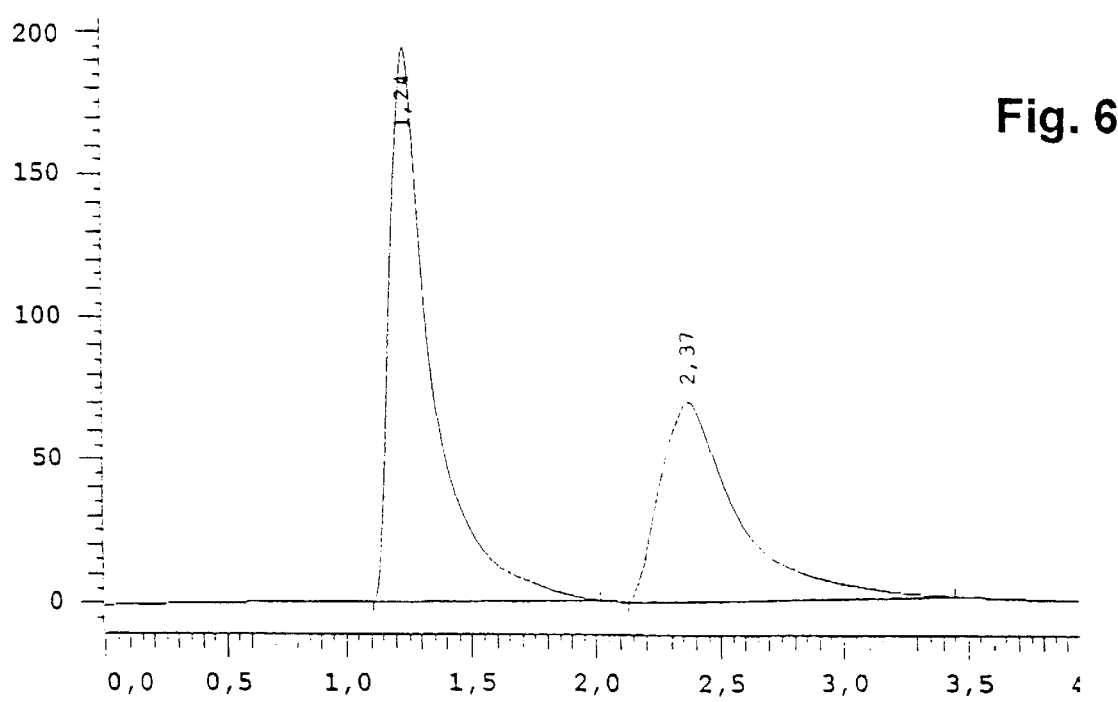
FIG. 6 shows the separation of dimethyl phthalate/dibutyl phthalate over a $C_{18}$ reverse phase.
Figure 7:
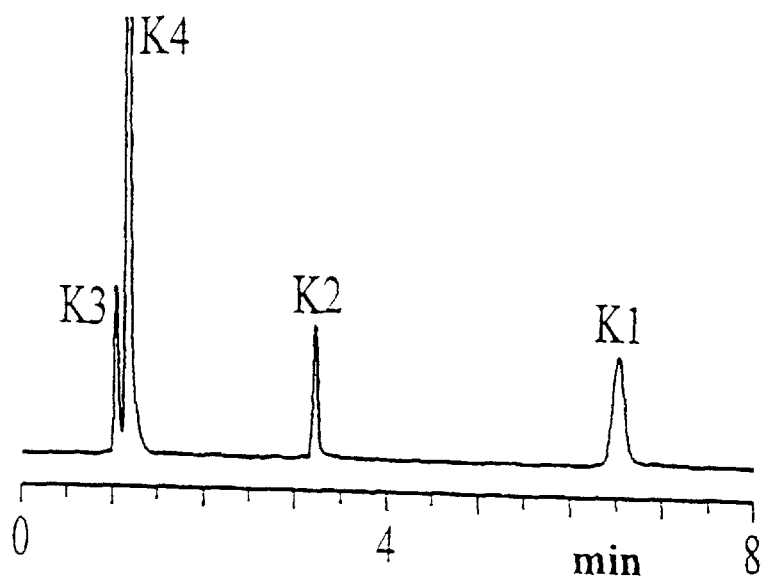
FIGS. 7A, 7B, and 7C depict elution curves of separation of various vitamins of the K group.
Figure 7:
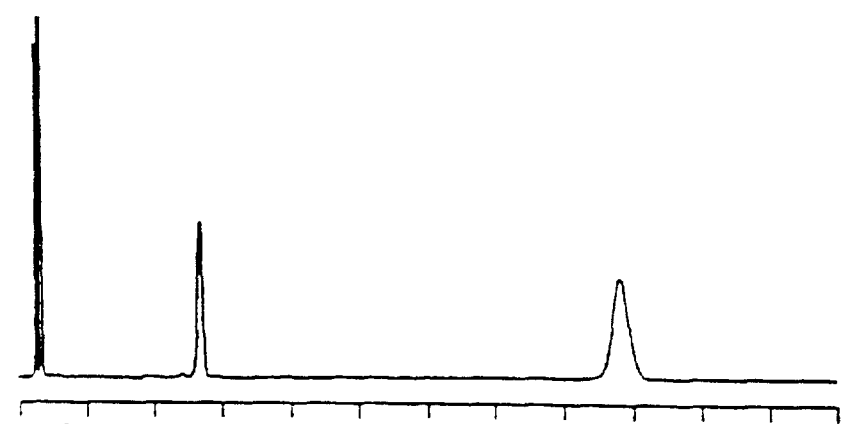
Figure 7:
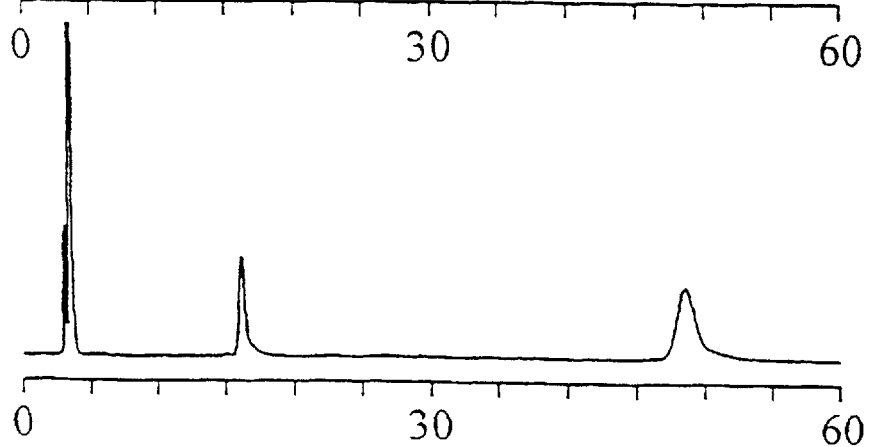

FIGS. 1 and 2 show separations of toluene, 2- and 3-nitroacetanilide over two unmodified monolithic sorbents having different pore sizes of the macropores, produced as described in PCT/EP97/06/980; for experimental details see Example B1. FIG. 3 shows the separation of the enantiomers of 2,2,2-trifluoro-1-anthrylethanol on the chiral monolithic sorbent (Pirkle-type) produced as described in Example A3; for experimental details see Example B4. FIG. 4 shows the resolution of racemic chromakalim over a sorbent containing chemically bound β-cyclodextrin (for production see Example A5; for experimental details see Example B6). FIG. 5 shows a preparative separation of a test mixture of toluene, 2-nitroacetanilide and 3-nitroacetanilide at different flow rates of the mobile phase (FIG. 5a: 40 ml/min; FIG. 5b: 130 ml/min;

FIG. 5c: 200 ml/min). Experimental details are described in Example B9. FIG. 6 shows the separation of dimethyl phthalate/dibutyl phthalate over a $C_{18}$ reverse phase. Experimental details are described in Example B10. FIG. 7 depicts elution curves of separations of various vitamins of the vitamin K group:

a) separation according to the invention (isocratic, flow-gradient chromatography using a monolithic sorbent);

b) isocratic using a monolithic sorbent;

c) isocratic using a particulate sorbent.

The curves b) and c) serve for comparison. Experimental details are described in Example B11.

Monolithic sorbents are known in principle from the literature; they include, in particular, porous ceramic shaped bodies as are disclosed in WO 94/19 687 and in EP 0 710 219. Particular preference is given to monolithic sorbents based on the porous shaped bodies which have interconnected macropores and also mesopores in the walls of the macropores, where the diameter of the macropores has a median value greater than 0.1 μm and the diameter of the mesopores has a median value of from 2 to 100 nm. However, only porous ceramic shaped bodies having a diameter of about 5 mm or less can be reproducibly obtained by the production process disclosed in the abovementioned publications. A similar restriction applies to the range of the macropores: the shaped body can be produced reproducibly only with macropores up to about 1 μm in diameter by the production process disclosed in the abovementioned publications. For preparative applications, larger shaped bodies (diameter about 1 cm or above) having larger macropores are preferably used. Such improved porous shaped bodies can, in particular, be obtained by processes as are disclosed in the patent application PCT/EP97/06 980. The process disclosed by PCT/EP97/06980 comprises:

(a) Dissolving a water-soluble polymer or some other pore forming agent and a precursor for a matrix dissolving agent in a medium that promotes the hydrolysis of the metalorganic compound (see step b);

(b) mixing a metalorganic compound which contains hydrolysable ligands to promote hydrolysis reaction;

(c) solidifying the mixture through the sol-gel transition, whereby a gel is prepared which has three dimensional interconnected phase domains one rich in solvent the other rich in inorganic component in which surface pores are contained;

(d) setting the matrix dissolving agent free from its precursor, whereby the matrix dissolving agent modifies the structure of said inorganic component;

(e) removing the solution by evaporation drying and/or heat-treatment;

(f) calcinating the gel to form the porous material.

These processes allow the reproducible production of larger shaped bodies having larger macropores. Preference is given to monolithic sorbents based on porous shaped bodies whose macropores have diameters in the range from 2 to 20 μm, in particular from 5 to 20 μm (in each case median values), and whose mesopores have diameters in the range from 2 to 100 nm (median values). Particular preference is given to monolithic sorbents according to the invention based on porous shaped bodies whose macropores have diameters in the range from 10 to 20 μm (in each case median values) and whose mesopores have diameters in the range from 2 to 100 nm (median values).

Monolithic sorbents used according to the invention comprise inorganic materials as are customary for particulate sorbents. In many cases (e.g. $SiO_2$), these sorbents can be readily used for chromatographic separations. However, these supports are more frequently modified in order to improve the separation properties; this is achieved by introducing additional groups which may be summarized under the term separation effectors.

Separation effectors and methods of introducing them into the support are essentially know to those skilled in the art. Examples of reactions by means of which separation effectors can be introduced are:

a) Modification with silane derivatives of the formula 1

$$SiX_nR^1_{(3-n)}R^2 \qquad \qquad I$$

where
X is a reactive group such as methoxy, ethoxy or halogen,
$R^1$ is $C_1$–$C_5$-alkyl,
n is 1, 2 or 3
and
$R^2$ has one of the following meanings:
  a1) unsubstituted or substituted alkyl or aryl, e.g. n-octadecyl, n-octyl, benzylpropyl or cyanopropyl;
  a2) an anionic or acid radical such as carboxypropyl;
  a3) a cationic or basic radical such as aminopropyl, diethylaminopropyl or triethylammoniumpropyl;
  a4) a hydrophilic radical such as (2,3-dihydroxypropyl) oxypropyl;
  a5) an activated radical which can form a bond, e.g. (2,3-epoxypropyl)oxypropyl;

b) Adsorption or chemical binding of polymers such as polybutadiene, siloxanes, polymers based on styrene/divinylbenzene, on (meth)acrylic acid derivatives or on other vinyl compounds, and also of peptides, proteins, polysaccharides and polysaccharide derivatives on the support.

c) Chemical binding of polymers mentioned under b) via the derivatives mentioned under a); these include graft polymers of poly(meth)acrylic acid derivatives on diol-modified silica gel as described in EP-B-0 337 144.

d) Adsorption or chemical binding of chiral phases such as amino acid derivatives, peptides or proteins, or of cyclodextrins, polysaccharides or polysaccharide derivatives.

Further customary modification possibilities and modification methods are known to those skilled in the art and are described in relevant manuals such as Unger, K.K. (ed) Porous Silica, Elsevier Scientific Publishing Company (1979) or Unger, K.K. Packings and Stationary Phases in Chromatographic Techniques, Marcel Dekker (1990).

Further examples of various separation effectors and of methods of introducing the separation effectors into monolithic sorbents are given in the following publications:

a) DE 38 11 042 discloses, inter alia, monomers which are suitable for preparing ion exchangers; these include, for example, acrylic acid, N-(sulfoethyl)-acrylamide, 2-acrylamido-2-methylpropane-sulfonic acid, N,N-dimethylaminoethylacrylamide, N,N-diethyl-aminoethylacrylamide and trimethylammoniumethyl-acrylamide.

Other monomers mentioned in this publication allow the binding of affinity ligands or of enzymes, or are suitable for reverse phase chromatography; these include, for example, acrylic acid, acrylamide, allylamine and acrylonitrile.

b) DE 43 10 964 discloses monomers containing an oxirane ring, an azlactone ring or a group which can be converted into an azlactone ring. Polymers containing such monomers are particularly well suited for binding affinity ligands or enzymes.

Affinity ligands are disclosed by way of example in DE 43 10 964.

Furthermore, the epoxide groups in such polymers can be advantageously reacted further, by which means ion exchangers, thiophilic sorbents or sorbents for metal chelate chromatography or hydrophobic chromatography are provided. Here, for example phosphoric acid, ammonia, diethylamine, trimethylamine, sulphurous acid or complexing agents such as iminodiacetic acid are added onto the oxirane ring.

The preparation of thiophilic sorbents and of sorbents for metal chelate chromatography is disclosed in DE 43 10 964.

DE 43 33 674 and DE 43 33 821 disclose reactions of this type by means of which ion exchangers can be produced.

DE 43 23 913 describes sorbents for hydrophobic interaction chromatography.

A large number of chiral separation materials for the separation of enantiomers are known in the prior art. These are exclusively particulate separation materials. The known chiral separation materials comprise either the chiral compound itself (for example cellulose triacetate) or else a chiral separation effector is applied to a support or chemically bound to a support (e.g. chemically bound amino acid derivatives). Moreover, it is possible to add chiral separation effectors which interact with a stationary phase to the eluant (dynamic coating with, for example, cyclodextrins).

Many chiral separation effectors are known; the most important groups of known chiral separation effectors are:
a) amino acids and their derivatives, e.g. L-phenylalanine, or D-phenylalanine, esters or amides of amino acids or acylated amino acids or oligopeptides;
b) natural and synthetic polymers having asymmetry or dissymmetry in the main chain; these include proteins (e.g. acid $\alpha_1$-glycoprotein, bovine serum albumin, cellulase; see J. Chrom. 264, pages 63–68 (1983), J. Chrom. 269, pages 71–80 (1983), WO 91/12 221), cellulose and cellulose derivatives and also other polysaccharides and their derivatives (e.g. cellulose tribenzoate, cellulose tribenzyl ether, cellulose trisphenylcarbamate, cellulose-tris-3-chlorobenzoate, amylose tris(3,5-dimethylphenylcarbamate), cellulose tris( 3,5-dimethylbenzoate), cellulose-tris(3,5-dimethylphenylcarbamate); see EP 0 147 804, EP 0 155 637, EP 0 718 625);
c) cyclodextrins and their derivatives (e.g. J. High Resol. Chrom. & Chromat. Comm. 3, pages 147–148 (1984); EP 0 407 412; EP 0 445 604);
d) polymers having asymmetric centres in the side chain (e.g. EP 0 249 078; EP 0 282 770; EP 0 448 823).
e) polymers containing voids which represent an imprint of the analyte (imprinted polymers; WO 93/09 075).

The enantiomerically pure chiral separation effectors can be adsorbed on a suitable support, if appropriate after modification. It is also possible to bind the enantiomerically pure chiral separation effectors to the support, if appropriate after introduction of suitable functional groups. Bifunctional reagents can also be used for this purpose. Reactions suitable for these process variants are known to those skilled in the art and described in relevant manuals. Shaped bodies containing chiral separation effectors which are suitable for the purposes of the invention are mentioned in the examples.

Further details regarding the preparation of various sorbents and their use may be found in the abovementioned publications; the relevant disclosure in these publications is incorporated by reference into the present application.

The abovementioned monolithic sorbents may be present in material separation apparatus which can be handled essentially like chromatographic columns. The known separation methods can be employed: batch processes, continuous processes, e.g. the simulated moving bed (SMB) process, or other countercurrent processes as are disclosed, for example, in U.S. Pat. No. 5,630,943.

It has been found that when using these preferred sorbents the flow rate can be varied over a wide range without the separation properties being adversely affected thereby. Utilization of this property makes it possible to match the flow rate to the elution profile without the separation performance being reduced. This can greatly decrease the time required for the separation, thus giving great advantages, particularly for preparative separations. The low pressure drop at a high flow rate is also relevant for use of the SMB process, since in this process a number of columns are connected in series. In addition, variation of the flow rate (flow gradient) makes it possible to match the resolving power to the separation problem (see Example B11).

Even without any further explanations, it is assumed that a person skilled in the art can make use of the above description in its widest scope. The preferred embodiments and examples are therefore to be regarded merely as descriptive but in no way limiting disclosures.

The complete disclosure of all applications, patents and publications mentioned above and below, and also the corresponding applications DE 197 25 639.2 filed on Jun. 18, 1997, DE 197 26 151.5 filed on Jun. 20, 1997, DE 197 26 152.3 filed on Jun. 20, 1997 and DE 198 01 575.5 filed on Jan. 19, 1998, are incorporated by reference in the present application.

EXAMPLES

The following examples serve to illustrate the invention; they do not constitute any restriction of the scope of the invention.

Hereinafter, room temperature is a temperature in the range from 15 to 30° C.

A PREPARATIVE EXAMPLES

Preparative Example A1

Preparation of a Monolithic Sorbent Modified with a $C_{18}$ Reverse Phase

A porous shaped body (83×7.2 mm; 2 μm pore size) comprising $SiO_2$ and produced as described in PCT/EP97/06 980 is reacted by standard methods with methyloctadecyldichlorosilane as silane derivative and subsequently subjected to an end-capping reaction; for these reactions, the reaction solutions are pumped through the shaped body.

This gives an RP-18-modified monolithic separation material. In an analogous way, RP-18-modified monolithic separation materials having dimensions of 93×25 mm and containing macropores having a diameter of 2 or 6 μm (median values) are obtained.

Preparative Example A2

Preparation of a Monolithic Sorbent Modified with Amino Groups

A porous shaped body (83×7.2 mm, 2 μm pore size) produced as described in PCT/EP97/06 980 is converted into a sorbent modified with amino groups according to standard methods by pumping a solution of aminopropyltrimethoxysilane in toluene through it.

Preparative Example A3

Preparation of a Monolithic Sorbent Modified with (R)-(-)-N-(2,4-dinitrobenzoyl)phenylglycine (Pirkle-type Modified Chiral Sorbent)

The porous shaped body modified with amino groups produced as described in Example A2 is reacted further by pumping a solution of (R)-(-)-N-(2,4-dinitrobenzoyl) phenylglycine and N-ethoxycarbonyl- 2-ethoxy-1,2-dihydroquinoline (EEDQ) in toluene through it. This gives a chiral sorbent.

Preparative Example A4
Preparation of a Monolithic Sorbent Modified with Ethyl N-acryloyl-L-phenylalanine as Monomer Units A porous shaped body (83×7.2 mm, 2 μm pore size) produced as described in EP 0 710 219 is converted into a chirally modified sorbent by pumping a) a solution of 3-glycidyloxypropyltrimethoxysilane in toluene and b) a solution of ethyl N-acryloyl-L-phenylalanine in toluene through it with addition of azobisisobutyronitrile (AIBN).

This gives a modified monolithic shaped body on which covalently bound ethyl L-phenylalanine groups are present as separation effectors.

Preparative Example A5
Preparation of a Chiral, Monolithic Sorbent to which β-cyclodextrin is Chemically Bound A porous shaped body produced as described in PCT/EP97/06 980 is, using a method analogous to that described in Example 2 of EP 0 445 604, reacted with a reaction solution of β-cyclodextrin, p-nitrophenyl chloroformate and 3-(2-aminoethyl)aminopropyltrimethoxysilane to give a chiral sorbent containing chemically bound β-cyclodextrin. For this purpose, the reaction solution is pumped through the shaped body.

A modified monolithic shaped body on which β-cyclodextrin is chemically bound is obtained.

B USE EXAMPLES

Use Example B1
Separation of Toluene, 2-Nitroacetanilide and 3-Nitroacetanilide over Monolithic Sorbents having Different Diameters of the Macropores Porous monolithic shaped bodies of $SiO_2$ (83×7.2 mm) having different diameters of the macropores (2 and 6 μm were produced as described in PCT/EP97/06 980. A solution of toluene, 2- and 3- nitroacetanilide is applied and separated using heptane/dioxane 80:20 as eluant (flow rate: 8 ml/min; UV detection).

The elution curves are shown in FIGS. 1 (2 μm pore size) and 2 (6 μm pore size).

Use Example B2
Separation of Dimethyl Phthalate and Dibutyl Phthalate over a Monolithic Sorbent Modified with a $C_{18}$ Reverse Phase A solution of dimethyl phthalate and dibutyl phthalate is applied to a column containing a monolithic sorbent produced as described in Example A1 and separated using methanol/water 90:10 as eluant (flow rate 4 ml/min; UV detection).

The substances are eluted separately.

Use Example B3
Separation over a Monolithic Sorbent Modified with Amino Groups A solution of xylose, fructose, glucose and sucrose is applied to the aminopropyl trimethoxysilane-modified sorbent produced as described in Example A2 and separated using acetonitrile/water 80:20 as eluant (flow rate: 4 ml/min; RI detection).

The saccharides were eluted separately.

Use Example B4
Separation over a Monolithic Sorbent Modified with (R)-(−)-N-(2,4-Dinitrobenzoyl)phenylglycine (Pirkle-type Modified Chiral Sorbent)

The enantiomers of 2,2,2-trifluoro-1-anthrylethanol are separated on the chiral Pirkle-type sorbent produced as described in Example A3 using heptane/i-propanol 99.5:0.5 (flow rate: 8 ml/min; UV detection).

The elution curve is shown in FIG. 3.

Use Example B5
Separation over a Monolithic Sorbent Modified with Ethyl N-acryloyl-L-phenylalanine as Monomer Units The enantiomers of chlorthalidone are separated on the chiral sorbent produced as described in Example A4 (conditions: heptane/dioxane 50:50; 4 ml/min; UV detection).

Use Example B6
Separation of Racemic Chromakalim over a Chiral Sorbent Containing Chemically Bound β-Cyclodextrin A modified monolithic shaped body (83×7.2 mm) produced as described in Example A5 is employed as sorbent and racemic chromakalim is separated under the following conditions:

Sample: Chromakalim (0.2 mg/ml in ethanol) Injection volume: 5 μl

Eluant: Methanol/water (20/80; v/v)

Temperature: Room temperature

Flow: 1.0 ml/min

Detection: 254 nm

The elution curve is shown in FIG. 4.

Use Example B7
Separation of Racemic Chlorthalidone with Dynamic β-Cyclodextrin Coating A modified monolithic shaped body (RP-18; 83×7.2 mm) produced as described in Example A1 is employed as sorbent and racemic chlorthalidone is separated under the following conditions:

Sample: Chlorthalidone (0.44 mg/ml) Injection volume: 5 μl

Eluant: Methanol/aqueous 25 mM sodium phosphate solution (pH 2) containing 10 mM β-cyclodextrin (20/80; v/v)

Temperature: Room temperature

Flow: 1.0 ml/min

Detection: 254 nm

The enantiomers are eluted separately.

Use Example B8
Separation of Racemic Prominal Using Dynamic β-Cyclodextrin Coating A modified monolithic shaped body (RP-18; 83×7.2 mm) produced as described in Example A1 is employed as sorbent and racemic prominal is separated under the following conditions:

Sample: Prominal (0.55 mg/ml) Injection volume: 5 μl

Eluant: Methanol/aqueous 25 mM sodium phosphate solution (pH 2) containing 10 mM β-cyclodextrin (20/80; v/v)

Temperature: Room temperature

Flow: 1.0 ml/min

Detection: 254 nm

The enantiomers are eluted separately.

Use Example B9
Separation of Toluene, 2-Nitroacetanilide and 3-Nitroacetanilide at Various Flow Rates A sample containing toluene, 2-nitroacetanilide and 3-nitroacetanilide is separated at different flow rates of the mobile phase:

Conditions:

Sorbent: Monolithic sorbent (SiO$_2$; 93×25 mm) (produced as described in PCT/EP97/06 980)

Mobile Phase: n-heptane/dioxane (90/10; v/v)

Sample volume: 40 µl

Detection: UV 254 nm

Flow rate: 40, 130, 200 ml/min.

|  | FIG. 5a | FIG. 5b | FIG. 5c |
|---|---|---|---|
| Flow rate [ml/min] | 40 | 130 | 200 |
| Number of theoretical plates [N] for 2-nitroacetanilide | 503 | 524 | 495 |
| Number of theoretical plates [N] for 3-nitroacetanilide | 465 | 465 | 445 |
| Pressure [bar] | 9 | 35 | 55 |

The results are summarized in FIGS. 5a–5c. The customary flow rate through a column having a diameter of 25 mm and packed with a particulate sorbent is 40 ml/min. The non-particulate supports thus allow a significantly higher operating rate which leads to significantly improved economics of the separation tasks.

Use Example B10

Determination of the Process Parameters for an SMB Separation of Dimethyl Phthalate and Dibutyl Phthalate Dimethyl phthalate and dibutyl phthalate are applied in various amounts and separated (see FIG. 6):

Conditions:

Sorbent: Monolithic sorbent (C$_{18}$-RP-modified SiO$_2$; 93×25 mm; produced as described in PCT/EP97/06 980, modified as described in Example A2)

Mobile phase: Methanol/water (80/20; v/v)

Sample volume: 50, 100, 300, 600 µl

Detection: UV 300 nm

Flow rate: 40 ml/min

For the components A (dimethyl phthalate) and B (dibutyl phthalate), the following modified Langmuir isotherms were found:

$$\overline{C}_A = 1,1 \cdot C_A + \frac{0,0735 \cdot C_A}{1 + 0,000735 \cdot C_A + 0,0175 \cdot C_B}$$

$$\overline{C}_B = 1,1 \cdot C_B + \frac{1,75 \cdot C_B}{1 + 0,000735 \cdot C_A + 0,0175 \cdot C_B}$$

The separation conditions for the SMB separation were determined from the above isotherms by the method described in R. M. Nicoud, F. Charton, J. Chromatogr. 702 (1995) 97 with the aid of the simulation software HELP:

| Column dimensions [mm] | 93 × 25 |
|---|---|
| Number of columns | 8 |
| Flow rate of feed [ml/min] | 1.9 |
| Feed concentration [g/l] | 320 + 320 |
| Flow rate of recycle stream [ml/min] | 44.1 |
| Flow rate of raffinate [ml/min] | 2.9 |
| Flow rate of extract [ml/min] | 21.8 |
| Cycle switching time [min] | 2.24 |
| Concentration in raffinate [g/l] | 209.7 |
| Concentration in extract [g/l] | 27.89 |
| Purities in raffinate/extract | >99.9 |

Use Example B11

Separation of Various Vitamins of the Vitamin K Group

A mixture of vitamins of the K group, containing the vitamins K$_1$, K$_2$, K$_3$ and K$_4$, is dissolved in acetonitrile/water (95:5; v/v). 10 µl of this solution are applied to a monolithic column (silica gel, RP-18-modified; 83×7.2 mm). Subsequently, a flow gradient is employed:

| Minutes | Flow rate (ml/min) |
|---|---|
| 0.0–1.5 | 3.0 |
| 1.5–3.0 | 3.0–9.5 |
| 3.0–8.0 | 9.5 |

The elution curve is shown in FIG. 7a) (Detection: UV at 280 nm).

For comparison, FIG. 7b) shows an elution curve at constant flow rate (1 ml/min) (sorbent as above). FIG. 7c) shows, as a further comparison, the elution curve using a particulate sorbent (LiChrospher RP 18; 1 ml/min).

C COMPARATIVE EXAMPLES

Comparative Example C1

Comparison of Separation Over a Particulate Sorbent with Separation Over a Monolithic Sorbent The productivity of LiChrospher® Si 100 15 µm sorbent is compared with that of a monolithic sorbent produced as described in PCT/EP97/06 980. The monolithic sorbent contains mesopores having a pore size of 10 nm, exactly like the commercial particulate sorbent LiChrospher®. The particle size of the LiChrospher® Si 100 is 15 µm. The monolithic sorbent has a skeleton size of 1.5–2 µm and 6 µm macropores.

For the particulate sorbent, the following characteristics were found:

$$\frac{\Delta P}{L} \text{ (bar/m)} = 26540 \times u(\text{m/sec})$$

(bar/m)=26540×u (m/sec)

H(m)=0.03657×u(m/sec)+5.5×10$^5$ for u>2.10$^3$ m/sec

For the monolithic sorbent, the following characteristics were found:

$$\frac{\Delta P}{L} \text{ (bar/m)} = 8500 \times u(\text{m/sec})$$

(bar/m)=8500×u (m/sec)

H(m)=0.00403×u(m/sec)+1.8×10$^{-5}$ for u>2×10$^{-3}$ m/sec

The best productivity is achieved when operating exactly at the desired number of theoretical plates at maximum pressure drop. The optimum eluant velocity and column length are then:

|  | Particulate sorbent (LiChrospher ® Si 100 15 μm) | Monolithic sorbent (6 μm pore diameter) |
|---|---|---|
| Eluant velocity (cm/min) | 23.1 | 132.4 |
| Column length (cm) | 98.0 | 53.3 |

The velocity over the monolithic sorbent is thus 5.7 times that over the particulate sorbent. The productivity (g/day) is then increased by a factor of 4 for the same column diameter. Since the column length required is shorter, the relative productivity (g/day/L of stationary phase) is increased by a factor of 10.5.

What is claimed is:

1. A process for preparative chromatographic separation of at least two substances, comprising chromatographically separating said at least two substances using a monolithic sorbent based on shaped $SiO_2$ bodies, wherein said bodies have macropores with a median diameter of 2 to 20 μm and mesopores with a median diameter from 2 to 100 nm, wherein said bodies are prepared by:
   a) dissolving a water-soluble polymer or some other pore forming agent and a precursor for a matrix dissolving agent in a medium that promotes the hydrolysis of metalorganic compounds;
   b) mixing a metalorganic compound which contains hydrolysable ligands in the medium to promote a hydrolysis reaction thereof
   c) solidifying the mixture through the sol-gel transition, whereby a gel is prepared which has three-dimensional interconnected phase domains, one rich in solvent and the other rich in an inorganic compound in which surface pores are contained;
   d) setting the matrix dissolving agent free from its precursor, whereby the matrix dissolving agent modifies the structure of said inorganic component; and
   e) calcining the gel to form the porous $SiO_2$ bodies.

2. A process according to claim 1, wherein said chromatographic separation is performed as a batch process.

3. A process according to claim 1, wherein said chromatographic separation is performed as a continuous process.

4. A process according to claim 1, wherein said bodies have macropores with a median diameter of 5 to 20 microns.

5. A process according to claim 1, wherein said bodies have macropores with a median diameter of 10 to 20 microns.

6. A process according to claim 1, wherein said $SiO_2$ bodies are modified to exhibit separation effectors.

7. A process according to claim 1, wherein said $SiO_2$ bodies are modified by reaction with a silane compound of formula I $$SiX_nR^1_{(3-n)}R^2 \qquad \qquad I$$

where
   X is methoxy, ethoxy or halogen,
   $R^1$ is $C_1$–$C_5$-alkyl,
   n is 1, 2 or 3; and
   R is n-octadecyl, n-octyl, benzylpropyl, cyanopropyl, carboxypropyl, aminopropyl, diethylaminopropyl, triethylammoniumpropyl, (2,3-dihydroxypropyl)oxypropyl, or (2,3-epoxypropyl)oxypropyl.

8. A process according to claim 7, wherein said $SiO_2$ bodies are modified by adsorption of polymers thereon or the chemical binding of polymers thereto, when said polymers are selected from polybutadiene, siloxanes, polymers based on styrene/divinylbenzene, polymers based on (meth)acrylic acid derivatives or other vinyl compounds, peptides, proteins and polysaccharides.

9. A process according to claim 1, wherein said $SiO_2$ bodies are modified by adsorption of polymers thereon or the chemical binding of polymers thereto, when said polymers are selected from polybutadiene, siloxanes, polymers based on styrene/divinylbenzene, polymers based on (meth)acrylic acid derivatives or other vinyl compounds, peptides, proteins and polysaccharides.

10. A process according to claim 1, wherein said $SiO_2$ bodies are modified by the adsorption thereon of chiral phases or the chemical binding of chiral phases thereto, wherein said chiral phases are selected from amino acid derivatives, peptides, proteins, cyclodextrins, or polysaccharides.

11. A process according to claim 1, wherein said $SiO_2$ bodies are modified with chiral separation effectors selected from amino acids, esters of amino acids, amides of amino acids, acylated amino acids and oligopeptides.

12. A process according to claim 1, wherein said process is a simulated moving bed process.

13. A process according to claim 1, wherein said $SiO_2$ bodies are modified by reaction with methyloctadecyldichlorosilane, and subsequently subjected to an end-capping reaction.

14. A process according to claim 1, wherein said $SiO_2$ bodies are modified with amino groups by passage of a solution of aminopropyltrimethoxysilane in toluene therethrough.

15. A process according to claim 1, wherein said $SiO_2$ bodies are modified with (R)-(−)-N-(2,4-dinitrobenzoyl) phenylglycine.

16. A process according to claim 1, wherein said $SiO_2$ bodies are modified with ethyl N-acryloyl-L-phenylalanine.

17. A process according to claim 1, wherein said $SiO_2$ bodies have β-cyclodextrin chemically bound thereto.

* * * * *